(12) United States Patent
Yim et al.

(10) Patent No.: US 11,224,400 B2
(45) Date of Patent: Jan. 18, 2022

(54) ULTRASONIC DIAGNOSTIC APPARATUS AND CONTROL METHOD THEREOF

(71) Applicant: SAMSUNG MEDISON CO., LTD., Gangwon-do (KR)

(72) Inventors: Yu Ri Yim, Seoul (KR); Chan Mo Kim, Seoul (KR); Eun Ho Yang, Seoul (KR); Gil Ju Jin, Seoul (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 368 days.

(21) Appl. No.: 16/353,661

(22) Filed: Mar. 14, 2019

(65) Prior Publication Data
US 2019/0290239 A1 Sep. 26, 2019

(30) Foreign Application Priority Data
Mar. 21, 2018 (KR) .................. 10-2018-0032528

(51) Int. Cl.
- *A61B 8/06* (2006.01)
- *A61B 8/00* (2006.01)
- *A61B 5/00* (2006.01)
- *A61B 8/08* (2006.01)

(52) U.S. Cl.
CPC .............. *A61B 8/06* (2013.01); *A61B 5/0053* (2013.01); *A61B 8/0891* (2013.01); *A61B 8/463* (2013.01); *A61B 8/469* (2013.01); *A61B 8/488* (2013.01); *A61B 8/5238* (2013.01); *A61B 8/54* (2013.01)

(58) Field of Classification Search
CPC ................................ A61B 8/06; A61B 8/0891
See application file for complete search history.

(56) References Cited

U.S. PATENT DOCUMENTS

| 5,730,136 A | 3/1998 | Laufer et al. |
| 2005/0159690 A1 | 7/2005 | Barak et al. |
| 2007/0270720 A1* | 11/2007 | Fry .......................... A61B 8/04 600/587 |

(Continued)

FOREIGN PATENT DOCUMENTS

| JP | 2003-28690 A | 1/2003 |
| JP | 2009-153919 A | 7/2009 |

(Continued)

OTHER PUBLICATIONS

Notification of Transmittal of the International Search Report and the Written Opinion of the International Searching Authority, or the Declaration issued in International Application No. PCT/KR2019/003272 dated Jul. 19, 2019.

(Continued)

*Primary Examiner* — Boniface N Nganga
(74) *Attorney, Agent, or Firm* — Morgan, Lewis & Bockius LLP

(57) ABSTRACT

An ultrasonic diagnostic apparatus includes a probe configured to irradiate an ultrasonic signal to an object and receive the ultrasonic signal reflected from the object; a pressure device configured to contract or expand a blood vessel of the object and is divided into a plurality of regions; and a controller configured to operate in one region of the plurality of regions to generate an image related to the blood vessel of the object and sequentially operate in other regions of the plurality of regions.

18 Claims, 17 Drawing Sheets

(56) References Cited

U.S. PATENT DOCUMENTS

| | | | |
|---|---|---|---|
| 2013/0144166 A1* | 6/2013 | Specht .................. | A61B 8/4444 600/441 |
| 2016/0120733 A1 | 5/2016 | Ishikawa et al. | |
| 2016/0338676 A1* | 11/2016 | Berger ................... | G16H 40/67 |
| 2018/0049482 A1 | 2/2018 | Erkus et al. | |

FOREIGN PATENT DOCUMENTS

| | | | |
|---|---|---|---|
| KR | 10-2011-0016510 A | 2/2011 | |
| KR | 10-2012-0059233 A | 6/2012 | |
| WO | 2006134754 A1 | 12/2006 | |
| WO | 2007/069155 A1 | 6/2007 | |

OTHER PUBLICATIONS

International Search Report issued in International Application No. PCT/KR2019/003272 dated Jul. 19, 2019.

Written Opinion of the International Searching Authority, or the Declaration issued in International Application No. PCT/KR2019/003272 dated Jul. 19, 2019.

Extended European Search Report dated Nov. 11, 2021 issued in European Patent Application No. 19772536.9.

* cited by examiner

ULTRASONIC DIAGNOSTIC APPARATUS AND CONTROL METHOD THEREOF

CROSS-REFERENCE TO RELATED APPLICATION(S)

This application is based on and claims priority under 35 U.S.C. § 119 to Korean Patent Application No. 10-2018-0032528, filed on Mar. 21, 2018 in the Korean Intellectual Property Office, the disclosure of which is incorporated by reference in its entirety.

TECHNICAL FIELD

Embodiments of the present disclosure relate to an ultrasonic diagnostic apparatus and a control method thereof, and more particularly, to an ultrasonic diagnostic apparatus that can perform a vascular regurgitation test more easily, and a control method thereof.

BACKGROUND

An ultrasonic diagnostic apparatus is an apparatus which irradiates ultrasonic waves toward a target point inside an object from the surface of the object, and receives echo ultrasonic waves reflected from the target point so as to non-invasively obtain a tomographic image of soft tissue of the object or an image of blood flow of the object.

The ultrasonic diagnostic apparatus has a compact size and is cheaper, compared to other medical imaging apparatuses, such as an X-ray imaging apparatus, a Computerized Tomography (CT) scanner, and a Magnetic Resonance Image (MRI) apparatus, and is widely used because it can display diagnosis images in real time.

The ultrasonic diagnostic apparatus includes a probe to transmit ultrasonic waves to the object and to receive echo ultrasonic waves reflected from the object, in order to obtain an ultrasonic image of the object.

Meanwhile, in a conventional ultrasonic diagnosis for examining a blood vessel of the object, an examiner manually evaluates the function of the blood vessel by inducing regurgitation of blood. In this case, the examiner has the inconvenience of placing the probe on the object with one hand and performing the squeezing and releasing with the other hand.

Further, even in the case of performing the squeegeeing and releasing with a pressing device such as a conventional blood pressure cuff, the examiner has to inconveniently carry out the test while continuously moving the pressing device.

SUMMARY

Therefore, it is an aspect of the present disclosure to provide an ultrasonic diagnostic apparatus for recognizing a position of a probe and sequentially pressing a part of an object according to a workflow, thereby eliminating a user's inconvenience and shortening a vascular regurgitation test time, and a control method thereof.

Additional aspects of the disclosure will be set forth in part in the description which follows and, in part, will be obvious from the description, or may be learned by practice of the disclosure.

In accordance with an aspect of the present disclosure, an ultrasonic diagnostic apparatus includes: a probe configured to irradiate an ultrasonic signal to an object and receive the ultrasonic signal reflected from the object; a pressure device configured to contract or expand a blood vessel of the object and is divided into a plurality of regions; and a controller configured to operate in one region of the plurality of regions to generate an image related to the blood vessel of the object and sequentially operate in other regions of the plurality of regions.

The pressure device may include a detector configured to detect a pressure transmitted by the probe. The controller may determine the one region of the pressure device based on a contact region of the probe transmitted by the detector.

The pressure device may be provided with a material capable of transmitting the ultrasonic signal irradiated by the probe.

The pressure device may contract or expand the blood vessel using at least one of voltage, air, fluid and oil.

The controller may generate a color Doppler image based on the ultrasonic signal transmitted by the probe and determine the presence or absence of regurgitation of blood and the regurgitation occurrence time based on the generated color Doppler image.

The controller may sequentially operate in the other regions of the plurality of regions based on a predetermined order and time after the color Doppler image is generated.

The ultrasonic diagnostic apparatus may further include: an inputter configured to receive an input command related to a test part of the object. The controller may determine a position of the pressure device based on the test part.

The controller may change the order of operating the other regions of the plurality of regions based on a user's command transmitted by the inputter.

The controller may adjust at least one of operation order, contraction strength, contraction time, expansion strength and expansion time of the pressure device based on a user's command transmitted by the inputter.

The ultrasonic diagnostic apparatus may further include: a display configured to display the generated image. The display may display a position of the probe determined based on the contact region of the probe.

In accordance with another aspect of the present disclosure, a control method of an ultrasonic diagnostic apparatus which comprises a pressure device divided into a plurality of regions includes: controlling the pressure device so that one region of the plurality of regions contracts or expands a blood vessel of an object; irradiating an ultrasonic signal to the object and receiving the ultrasonic signal reflected from the object; generating an image related to the blood vessel of the object based on the received ultrasonic signal; and re-controlling the pressure device so that other regions of the plurality of regions are sequentially operated in.

The pressure device may include a detector configured to detect a pressure transmitted by the probe. The controlling may include determining the one region of the pressure device based on a contact region of the probe transmitted by the detector.

The pressure device may be provided with a material capable of transmitting the ultrasonic signal.

The pressure device may contract or expand the blood vessel using at least one of voltage, air, fluid and oil.

The generating may include generating a color Doppler image based on the ultrasonic signal; and determining the presence or absence of regurgitation of blood and the regurgitation occurrence time based on the generated color Doppler image.

The controlling may include re-controlling the pressure device to sequentially operate in the other regions of the plurality of regions based on a predetermined order and time after the color Doppler image is generated.

The method may further include receiving an input command related to a test part of the object. The controlling may include determining a position of the pressure device based on the test part.

The controlling may include changing the order of operating the other regions of the plurality of regions based on a user's command.

The controlling may include adjusting at least one of operation order, contraction strength, contraction time, expansion strength and expansion time of the pressure device based on the input command.

The method may further include displaying the generated image. The displaying may include displaying a position of the probe determined based on the contact region.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Figure 1:
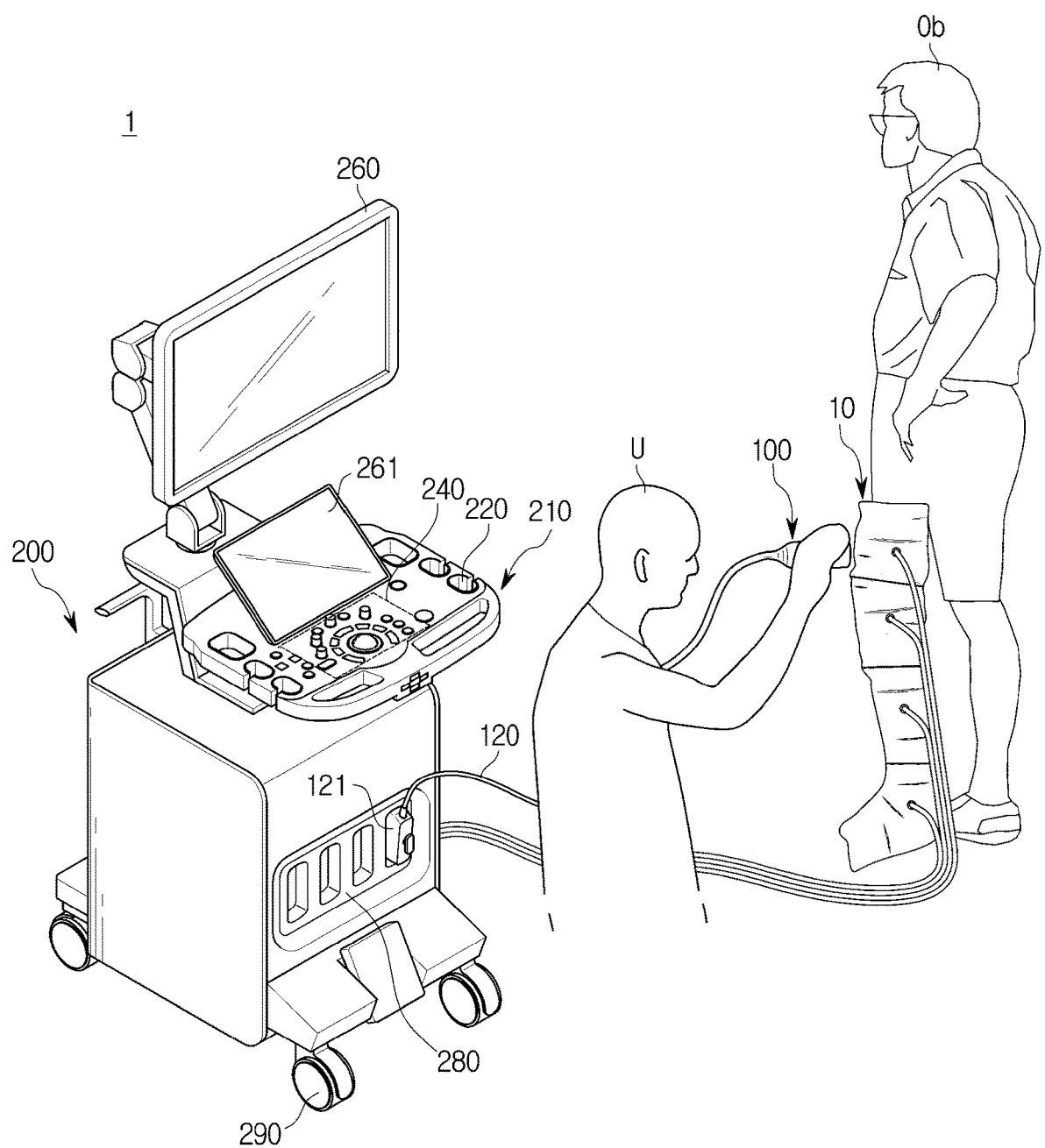
FIG. 1 is a view illustrating an appearance of an ultrasonic diagnostic apparatus according to an embodiment.

Configurations illustrated in the embodiments and the drawings described in the present specification are only the preferred embodiments of the present disclosure, and thus it is to be understood that various modified examples, which may replace the embodiments and the drawings described in the present specification, are possible when filing the present application.

Also, like reference numerals or symbols denoted in the drawings of the present specification represent members or components that perform substantially the same functions.

The terms used in the present specification are used to describe the embodiments of the present disclosure. Accordingly, it should be apparent to those skilled in the art that the following description of exemplary embodiments of the present disclosure is provided for illustrative purposes only and not for the purpose of limiting the disclosure as defined by the appended claims and their equivalents. It is to be understood that the singular forms "a," "an," and "the" include plural referents unless the context clearly dictates otherwise. It will be understood that when the terms "includes," "comprises," "including," and/or "comprising," when used in this specification, specify the presence of stated features, figures, steps, components, or combinations thereof, but do not preclude the presence or addition of one or more other features, figures, steps, components, members, or combinations thereof.

It will be understood that, although the terms first, second, etc. may be used herein to describe various components, these components should not be limited by these terms. These terms are only used to distinguish one component from another. For example, a first component could be termed a second component, and, similarly, a second component could be termed a first component, without departing from the scope of the present disclosure.

As used herein, the term "and/or" includes any and all combinations of one or more of associated listed items.

Also, the terms "front," "rear," "upper," and "lower," when used in this description, are defined based on the drawings, and the shapes and locations of the corresponding components are not limited by the terms.

Hereinafter, the embodiments of the present disclosure will be described in detail with reference to the accompanying drawings.

FIG. 1 is a view illustrating an appearance of an ultrasonic diagnostic apparatus according to an embodiment.

Referring to FIG. 1, an ultrasonic diagnostic apparatus 1 may include a main body 200, an ultrasonic probe 100 for transmitting an ultrasonic signal to an object Ob to be diagnosed and receiving a signal reflected from the object Ob, and a pressure device 10 for contracting or expanding a blood vessel of the object Ob.

First, the pressure device 10 may be divided into a plurality of regions, and may sequentially operate in one region to another region based on a signal transmitted from the main body 200. Particularly, each region of the pressure device 10 may be operated in to contract or expand the blood vessel of the object Ob based on the signal transmitted from the main body 200.

Here, the object Ob may be a human or an animal having the blood vessel, although not limited to these. That is, the object Ob may be anything whose internal structure can be imaged by the ultrasonic diagnostic apparatus 1.

The pressure device 10 may be attached to a lower body of the object Ob, as illustrated in FIG. 1. Hereinafter, the pressure device 10 is illustrated attached to the lower body of the object Ob to press the object Ob. However, the shape of the pressure device is not limited to that illustrated in FIG. 1, and may be formed in various shapes. Also, unlike FIG. 1, the pressure device 10 may be attached not only to the lower body limbs but also to the upper body of the object Ob, and may be changed into various shapes.

The pressure device 10 may expand one region of the plurality of regions using at least one of air, fluid and oil. When one region of the pressure device 10 is expanded, the blood vessel of the object Ob enclosed in one region may be contracted under pressure. Conversely, when one region of the pressure device 10 is contracted, the blood vessel of the corresponding object Ob may be expanded.

On the other hand, the pressure device 10 may expand or contract the blood vessel of the object Ob through air, fluid and oil as well as electrical shock.

The ultrasonic probe 100 may be positioned in one region of the pressure device 10 by a user U. The ultrasonic probe 100 may irradiate the ultrasonic signal through one area of the pressure device 10 and receive an echo ultrasonic signal reflected from the object Ob and passed through the pressure device 10. The ultrasonic probe 100 may include a transducer T for converting electrical signals into ultrasonic waves and vice versa, a male connector 121 physically coupled with a female connector 280 of the main body 200 and configured to transmit/receive signals to/from the main body 200, and a cable 120 connecting the transducer T to the male connector 121.

The transducer T may generate ultrasonic waves according to alternating-current power applied thereto. More particularly, the transducer T may receive alternating-current power from an external power supply or from an internal power storage unit, for example, a battery. A vibrator of the transducer T may vibrate according to the alternating-current power to generate ultrasonic waves.

One end of the cable 120 may be connected to the transducer T, and the other end of the cable 120 may be connected to the male connector 121, so as to connect the transducer T to the male connector 121. The male connector 121 may physically couple with the female connector 280 of the main body 200. The male connector 121 may transfer electrical signals generated by the transducer T to the female connector 280, or may receive control signals generated by the main body 200 from the female connector 280.

The main body 200 may receive an electrical signal transmitted from the transducer T through the cable 120 and output the electrical signal as an image.

The main body 200 may be provided with a holder 220 and the user U may store the ultrasonic probe 100 by holding the ultrasonic probe 100 with the holder 220 when the ultrasonic diagnostic apparatus 1 is not used. In FIG. 1, the holder 220 for holding the ultrasonic probe 100 is illustrated as being provided on a control panel 210. However, the holder 220 may be provided on the main body 200 according to the user's convenience. It is also possible that the holder 220 is provided on both the main body 200 and the control panel 210.

The main body 200 may be provided with a mobile device 290 so as to move the ultrasonic diagnostic apparatus 1. The mobile device 290 may be a plurality of casters provided on the bottom surface of the main body 200. The casters may be aligned to allow the main body 200 to run in a specific direction, or may be freely movably provided to be movable in an arbitrary direction or may be locked to stop at a specific position.

The main body 200 may include a display 260 and the control panel 210. The control panel 210 may be provided with an inputter 240 for the user U to control the ultrasonic diagnostic apparatus 1. The inputter 240 may receive various control commands such as setting information about the ultrasonic probe 100 and the operation order of the pressure device 10, from the user U.

For example, the setting information about the ultrasonic probe 100 may include gain information, zoom information, focus information, Time Gain Compensation (TGC) information, depth information, frequency information, power information, frame average information, and dynamic range information.

Also, the command about the operation order of the pressure device 10 may include an order of whether or not the blood vessel of the object Ob is contracted or expanded from any of the plurality of regions.

In addition, the inputter 240 may receive various commands and is not limited.

Meanwhile, the inputter 240 may be implemented as a mouse, a keyboard, a foot switch, or a foot pedal. For example, the keyboard may be hardwirily implemented. The keyboard may include at least one of a switch, a key, a joystick, and a trackball. According to another example, the keyboard may be softwirily implemented, like a Graphic User Interface (GUI). In this case, the keyboard may be displayed on the display 260. The foot switch or the foot pedal may be disposed below the main body 200, so that the user can control the operation of the ultrasonic diagnostic apparatus 1 using the foot pedal.

The display 260 may display an ultrasonic image of a target part of the object Ob. The ultrasonic image displayed on the display 260 may be a 2D ultrasonic image or a 3D ultrasonic image. The display 260 may display various ultrasonic images according to operation modes of the ultrasonic diagnostic apparatus 1. Also, the display 260 may display information related to an operation state of the ultrasonic probe 100, as well as a menu or guidance needed for ultrasonic diagnosis.

The display 260 may visually output the position of the ultrasonic probe 100 detected by the pressure device 10 through a plurality of regions of the pressure device 10 or icons exemplified by the object Ob.

Meanwhile, the display 260 may be implemented as a Cathode Ray Tube (CRT), a Liquid Crystal Display (LCD), a Light Emitting Diode (LED) display, a Plasma Display Panel (PDP) display, an Organic Light Emitting Diode (OLED) display, etc., which are well-known in the art.

An auxiliary display 261 may be provided on the control panel 210. The auxiliary display 261 may provide related information such as a menu or an auxiliary image for optimizing the ultrasonic image or may provide a graphical interface to the user U.

When the display 260 and the auxiliary display 261 are implemented as a touch screen type, the display 260 and the auxiliary display 261 may also perform the functions of the inputter 240. That is, the main body 200 may receive various commands from the user U through at least one of the display 260, the auxiliary display 261 and the inputter 240.

Although not illustrated in the figure, the main body 200 may be provided with a voice recognition sensor and may receive a voice command from the user U or may include other configurations not described.

Figure 2:
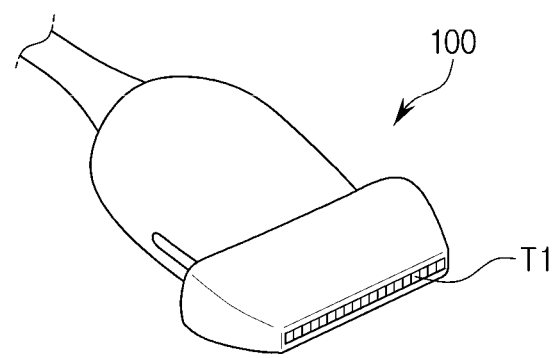
FIG. 2 is a view illustrating an appearance of an ultrasonic probe including a 1-Dimensional (1D) array transducer according to an embodiment.
Figure 3:
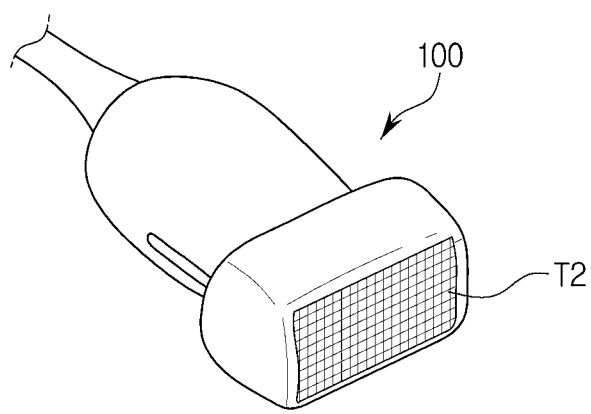
FIG. 3 is a view illustrating an appearance of the ultrasonic probe including a 2-Dimensional (2D) array transducer according to an embodiment.

FIG. 2 is a view illustrating an appearance of an ultrasonic probe including a 1-Dimensional (1D) array transducer according to an embodiment, and FIG. 3 is a view illustrating an appearance of the ultrasonic probe including a 2-Dimensional (2D) array transducer according to an embodiment. Hereinafter, the description will be made together to prevent duplication of description.

The ultrasonic probe 100 may contact the pressure device 10 to irradiate the object Ob with the ultrasonic signal.

Particularly, the ultrasonic probe 100 may irradiate the ultrasonic signal according to a control command signal transmitted from the main body 200. The ultrasonic probe 100 may include the transducer T for converting the ultrasonic signal into an electrical signal and vice versa according to the control command. The transducer T may be implemented as a 1D or 2D transducer array.

For example, the transducer T may include a 1D transducer array T1 as illustrated in FIG. 2. In another embodiment, the transducer T may include a 2D transducer array T2 as illustrated in FIG. 3.

Each of the transducer T elements constituting the transducer array may convert the ultrasonic signal into an electrical signal and vice versa. For this, the transducer T element may be a magnetostrictive ultrasonic transducer using the magnetostrictive effect of a magnetic material, a piezoelectric ultrasonic transducer or a piezoelectric Micromachined Ultrasonic Transducer (pMUT) using the piezoelectric effect of a piezoelectric material, or a capacitive Micromachined Ultrasonic Transducer (cMUT) that transmits and receives ultrasonic waves using vibration of several hundreds or thousands of micromachined thin films.

Meanwhile, the transducer T may be linearly aligned or may be convexly aligned. In both cases, the ultrasonic probe 100 may operate according to the same operation principle, however, when the ultrasonic probe 100 includes the convex transducer T in a convex shape, the ultrasonic waves irradiated from the transducer T may be in the shape of a fan, and accordingly, the ultrasonic image may also be created in the shape of a fan.

The transducer T of the ultrasonic probe 100 may include the 2D transducer array T2, as illustrated in FIG. 3. When the transducer T includes the 2D transducer array, the inside of the object Ob may be three-dimensionally imaged.

Each of the transducer T elements constituting the 2D transducer array T2 may be the same as each of the transducer T elements constituting the 1D transducer array T1, and accordingly, a detailed description thereof will be omitted.

Figure 4:
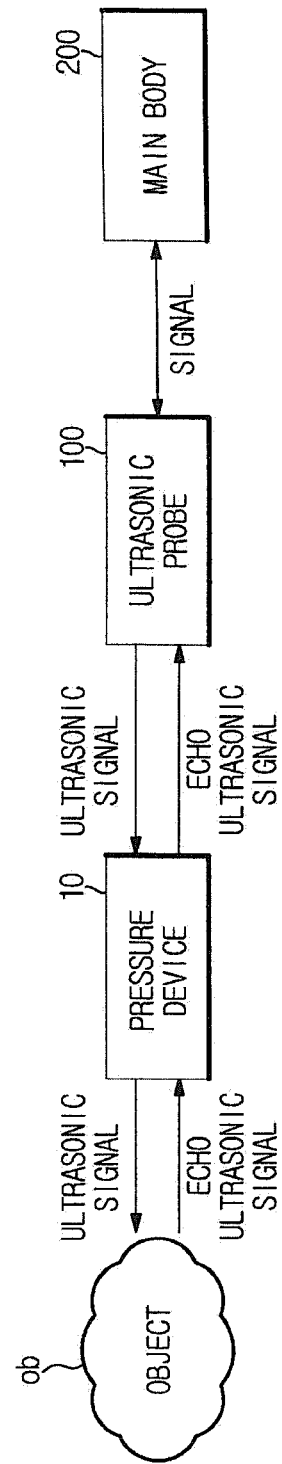
FIG. 4 is a view illustrating a relationship between a pressure device, an ultrasonic probe, and a main body according to an embodiment.

FIG. 4 is a view illustrating a relationship between a pressure device, an ultrasonic probe, and a main body according to an embodiment.

Referring to FIG. 4, the ultrasonic diagnostic apparatus 1 may include the pressure device 10, the ultrasonic probe 100 and the main body 200. The ultrasonic probe 100 may contact a region other than a region where the pressure device 10 contracts or expands the blood vessel and irradiate the ultrasonic signal toward the target part of the object Ob, i.e., the blood vessel.

For example, the ultrasonic probe 100 may irradiate a plane wave to the object Ob through the 2D transducer array T2. Here, the plane wave refers to the ultrasonic signal in the form of the 2D plane.

The ultrasonic probe 100 may convert the ultrasonic signal reflected from the object Ob, that is, the echo ultrasonic signal passed through the pressure device 10, into an electrical signal, and then transmit the electrical signal to the main body 200.

The main body 200 may non-invasively obtain a tomographic image of soft tissue of the object or an image of blood flow of the object based on the converted electrical signal and may provide it to the user U.

At this time, the main body 200 may include a main controller 250 (see FIG. 5) for performing an image processing process of converting the received echo ultrasonic signal into an ultrasonic image. The main controller 250 may be implemented in the form of hardware such as a processor and a graphic processor, or may be implemented in the form of software that can be executed on hardware. The operation of the main controller 250 will be described in detail later.

Meanwhile, the ultrasonic probe 100 may generate a direct ultrasonic image using the received echo ultrasonic signal, and then transmit the ultrasonic image generated by the main body 200.

The generated ultrasonic image may be stored in a memory 251 in the main body 200. In addition, the ultrasonic image may be stored in a web storage or a cloud server that performs a storage function on the web.

The ultrasonic diagnostic apparatus 1 may control the pressure device 10 divided into the plurality of regions to provide convenience for a regurgitation test of the blood vessel for long-time examination. To this end, the ultrasonic diagnostic apparatus 1 may sequentially operate in the plurality of regions on the basis of a predetermined workflow or the position of the ultrasonic probe 100.

In addition, the ultrasonic diagnostic apparatus 1 may generate a color Doppler image generated from the echo ultrasonic signal in order to shorten a test time, and determine the presence or absence of regurgitation and the regurgitation time of the blood based on the generated color Doppler image.

Hereinafter, the operation of the ultrasonic diagnostic apparatus 1 will be described in detail with reference to the internal configurations thereof.

Figure 5:
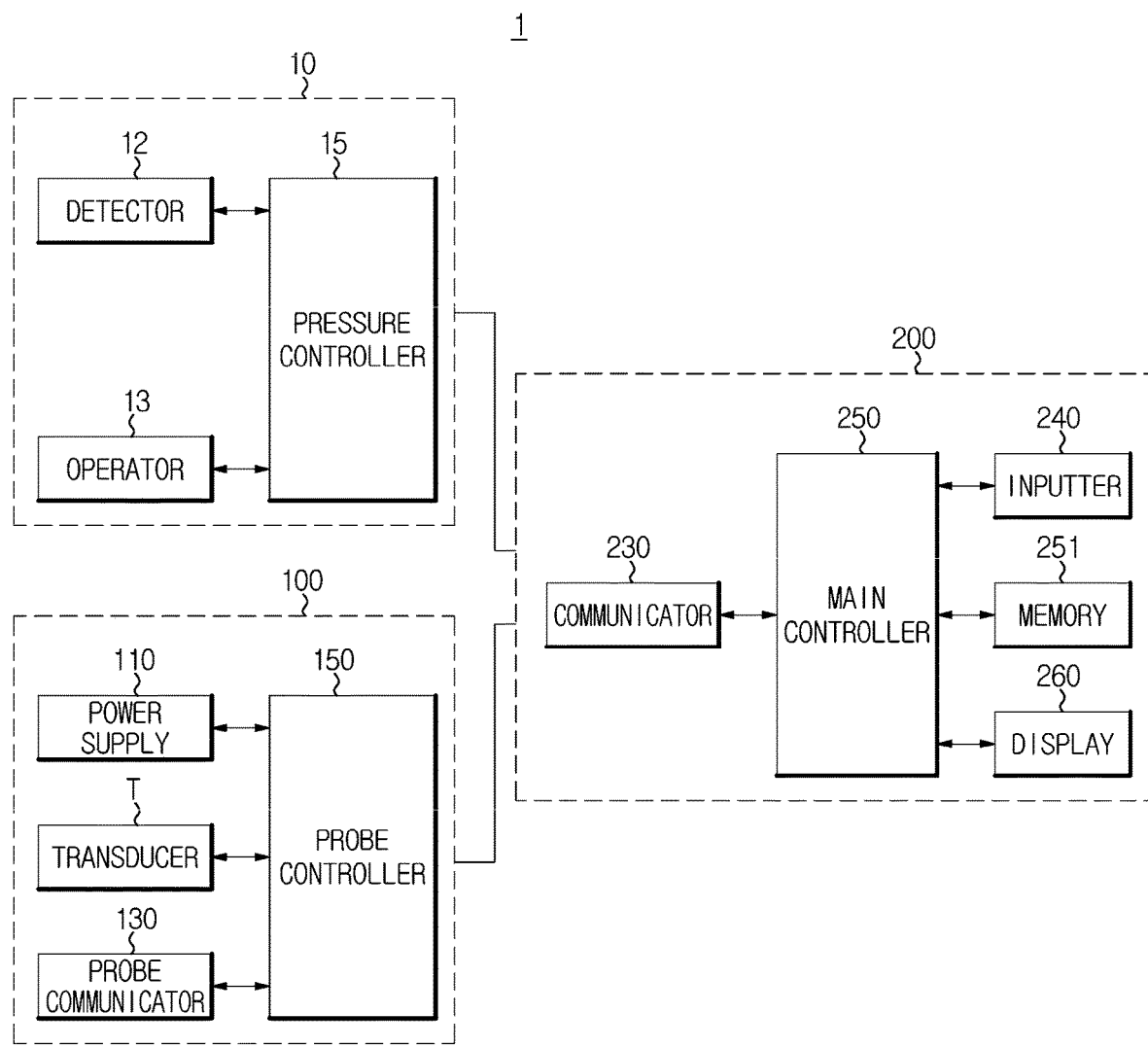
FIG. 5 is a control block diagram of the ultrasonic diagnostic apparatus according to an embodiment.

FIG. 5 is a control block diagram of the ultrasonic diagnostic apparatus according to an embodiment.

Referring to FIG. 5, the ultrasonic diagnostic apparatus 1 may include the pressure device 10, the ultrasonic probe 100 and the main body 200.

Particularly, the pressure device 10 may be composed of the plurality of regions, and include a detector 12 for detecting the ultrasonic probe 100 for each region, an operator 13 for expanding or contracting the blood vessel of the object Ob, and a pressure controller 15 for controlling the configurations.

The detector 12 may be provided with a sensor that detects a pressure generated by the user U positioning one of the plurality of regions with the ultrasonic probe 100, or a material that generates a signal by the pressure.

The operator 13 may contract or expand the blood vessel of the object Ob using at least one of voltage, air, fluid and oil based on the signal transmitted from the pressure controller 15. For example, the operator 13 may inject air, fluid or oil into one of the plurality of regions to expand or contract the region, thereby contracting or expanding the blood vessel. As another example, the operator 13 may apply an electric shock to the blood vessel in one region using the voltage to contract or expand the blood vessel. In addition, the operator 13 may contract or expand the blood vessel through various embodiments of the art.

The pressure controller 15 may sequentially operate in the plurality of regions under the control of the main body 200 to contract or expand the blood vessel.

The pressure controller 15 may transmit the signal transmitted from the detector 12 to the main body 200 or may determine whether the ultrasonic probe 100 is positioned in which of the plurality of regions. For example, when the pressure transmitted from the detector 12 is greater than or equal to a reference value, the pressure controller 15 may determine whether the ultrasonic probe 100 is positioned in the current region.

On the other hand, the pressure device 10 need not necessarily include a hardware chip such as the pressure controller 15, and may operate under the control of the main body 200. In this case, the pressure device 10 may consist only of the detector 12 and the operator 13.

The ultrasonic probe 100 may include a power supply 110 for supplying power to each configuration of the ultrasonic probe 100, the transducer T for receiving the echo ultrasonic signal reflected from the object Ob after irradiating the ultrasonic signal with the object Ob and converting the echo ultrasonic signal into an electrical signal, a probe communicator 130 for transmitting and receiving various signals to and from the main body 200 or an external device, and a probe controller 150 for controlling the overall operation of the ultrasonic probe 100.

First, the power supply 110 may supply power to the ultrasonic probe 100. Particularly, the power supply 110 may convert electrical energy into chemical energy and accumulate the chemical energy, and convert the accumulated chemical energy into electrical energy to supply power. The power supply 110 may be implemented as a lithium ion battery, a nickel metal hydride battery, a polymer battery, or the like. However, the power supply 110 is not limited to the above-described example. The power supply 110 may be embodied in various types of batteries that are built in the ultrasonic probe 100 and may supply power.

The power supply 110 may be charged through a wired charging method that directly connects to a charging apparatus, or through a wireless charging method. That is, the charging method of the power supply 110 may be performed according to various known methods, and the charging method is not limited.

When the ultrasonic probe 100 is connected to the main body 200 through the wired communication method, the power supply 110 may or may not be included in the ultrasonic probe 100 as needed, and is not limited to FIG. 5.

The transducer T has been described in FIGS. 1 to 3, and accordingly, a detailed description thereof will be omitted.

The probe communicator 130 may communicate with the main body 200 or the external device of the ultrasonic diagnostic apparatus 1 and may transmit the electrical signal converted by the transducer T. When the ultrasonic probe 100 generates the image based on the converted electrical signal, the ultrasonic probe 100 may transmit the generated image to the outside through the probe communicator 130.

The probe controller 150 may generate a control signal according to a control command of the user and may control the operation of the components of the ultrasonic probe 100 through the generated control signal. The transducer array included in the transducer T may combine the converted electrical signals to perform beamforming to perform a time delay.

That is, the probe controller 150 may include all the general operations or configurations performed by the ultrasonic probe 100, and may be a hardware processor or a memory that can be integrated into a system on chip (SOC).

The main body 200 may include a communicator 230 for communicating with the pressure device 10, the ultrasonic probe 100 and the outside of the ultrasonic diagnostic apparatus 1, the inputter 240 for receiving the users input command, the memory 251 for storing various data such as the generated image and the operation order of the pressure device 10, the display 260 for outputting the generated image, and the main controller for controlling the overall various configurations of the main body 200 and all of the configurations of the ultrasonic diagnostic apparatus 1.

Particularly, the communicator 230 may receive a result of the detection of the ultrasonic probe 100 transmitted by the pressure device 10, transmit a command for controlling the ultrasonic probe 100 to irradiate the ultrasonic signal on the object Ob, and receive the converted signal based on the echo ultrasonic signal.

In addition, the communicator 230 may transmit the ultrasonic image generated by the main controller 250 to the outside, and may receive a command that the user U transmits remotely through the external device.

Meanwhile, the communicator 230 may include one or more components to enable wireless communication or wired communication with the external device. For example, the communicator 230 may include at least one of a short-range communication module, a wired communication module, and a wireless communication module.

The short-range communication module may include various short-range communication modules to transmit/receive signals using a wireless communication network within a short distance range, such as a Bluetooth module, an infrared communication module, a Radio Frequency Identification (RFID) communication module, a WLAN communication module, an NFC communication module, and a Zigbee communication module.

The wired communication module may include various cable communication modules, such as a Universal Serial Bus (USB), High Definition Multimedia Interface (HDMI), Digital Visual Interface (DVI), Recommended Standard 232 (RS-232), Power Line Communication (PLC), and Plain Old Telephone Service (POTS), as well as various wired communication modules, such as a Local Area Network (LAN) module, a Wide Area Network (WAN) module, and a Value Added Network (VAN) module.

The wireless communication module may include wireless communication modules supporting various wireless communication methods, such as Global System for Mobile Communication (GSM), Code Division Multiple Access (CDMA), Wideband Code Division Multiple Access (WCDMA), Universal Mobile Telecommunications System (UMTS), Time Division Multiple Access (TDMA), and Long Term Evolution (LTE), as well as a Wi-Fi module and a Wireless broadband (Wibro) module.

The inputter 240 may receive at least one of various input commands from the user U. Particularly, the inputter 240 may include various start commands for performing the blood vessel test, commands for operating the plurality of regions provided in the pressure device 10, commands for entering a color Doppler mode, and commands for pulse wave or sample volume setting. In addition, the inputter 240 may receive various commands from the user U, and the disclosure is not limited to the above.

Meanwhile, the inputter 240 may be implemented in various hardware devices and provided in the control panel 210, and a detailed description thereof will be omitted.

The memory 251 may store a control program for controlling the components of the main body 200, an application or data for the entire operation of the ultrasonic diagnostic apparatus 1.

The memory 251 may previously store the order of controlling the plurality of regions of the pressure device 10 during the blood vessel test, store the detection result of the ultrasonic probe 100, and refer to the next test progress.

Further, the memory 251 may store a program (hereinafter referred to as a guide program) that can guide the diagnosis of the object Ob. In order to perform the blood vessel test through the ultrasonic diagnostic apparatus 1, the test should be carried out in the plurality of regions and accompanied by a detailed test step performed in each region. Accordingly, the memory 251 may provide the stored guide program to the main controller 250 for smooth progress of the user's test.

For example, the guide program may output the object Ob or one region of the pressure device 10 through the display 160 so that a first region of the plurality of regions is tested.

When the ultrasonic probe 100 is positioned in the first region where the user U is displayed, the main body 200 may control the pressure device 10 to operate in the region positioned below the first region. As a result, the blood vessel is contracted or expanded and the color Doppler image is formed. The guide program may guide the user U to proceed with the work of determining the regurgitation of the blood flow after the color Doppler image is generated.

In addition, the guide program may guide the user U to proceed with the test of a second region after the test of the first region has proceeded. The second region may include one region of the plurality of regions separated by the pressure device 10 except for the first region. The order of the first region and the second region may vary according to the position of the first region and may be based on a pre-stored order.

When the user U places the ultrasonic probe 100 in a third region instead of the second region presented by the guide program, the guide program may skip the second region and guide the test progress to the third region.

Meanwhile, the memory 251 may be implemented through at least one type of storage medium among a flash memory type, a hard disk type, a multimedia card micro type, card type memory (for example, Secure Digital (SD) memory or eXtreme Digital (XD) memory), RAM, Static Random Access Memory (SRAM), ROM, Electrically Erasable Programmable Read-Only Memory (EEPROM), Programmable Read-Only Memory (PROM), magnetic memory, a magnetic disk, and an optical disk. However, the memory 251 is not limited to the above-mentioned devices, and may be implemented as any other type of memory well-known in the art.

The display 260 may display information including the ultrasonic image generated through the image processing process from the echo ultrasonic signal. In the disclosed embodiment, the display 260 may output the color Doppler image as an example of the ultrasonic image. The display 260 may output an interface for one of the plurality of regions in which the pressure device 10 operates in and a test part of the object Ob in which the color Doppler image is generated.

In addition, the display 260 may display a color Doppler mode entry screen according to the progress of the test process, display a first test result screen including the presence/absence of regurgitation of blood and regurgitation time information, display a sample volume setting screen, and a second test result screen indicating a blood flow analysis result of the sample volume.

When the display 260 and the auxiliary display 261 are implemented as a touch screen type, the display 260 and the auxiliary display 261 may also perform the functions of the inputter 240. That is, the main body 200 may receive various commands from the user U through at least one of the display 260, the auxiliary display 261 and the inputter 240.

When the display 260 is implemented as the touch screen type, the display 260 may display a graphical user interface (GUI) to receive various control commands related to the ultrasonic probe 100 as well as the main body 200 from the user U. Accordingly, the display 260 implemented as the touch screen type may perform the function of the inputter.

An example of the screen displayed on the display 260 in accordance with the progress of the test process will be described later in the related part.

The main controller 250 (hereinafter referred to as the controller) may control the overall operation of the ultrasonic diagnostic apparatus 1 and the signal flow between the internal components of the ultrasonic diagnostic apparatus 1 and process the data.

The main controller 250 may generate an ultrasonic image from the electrical signal transmitted by the transducer T. For example, the main controller 250 may obtain an ultrasonic image by performing the image processing process based on the control data stored in the memory 251, with respect to the echo ultrasonic signal received through the transducer T.

The ultrasonic image is a gray scale image obtained by scanning the object Ob according to one of an Amplitude-mode (A-mode), a Brightness-mode (B-mode), and a Motion-mode (M-mode).

In addition, the ultrasonic image may include a color Doppler image that expresses the motion of the object Ob using a Doppler effect according to a Color Doppler mode (C-mode), and may also include a spectral Doppler image that provides a Doppler spectrum according to a Doppler mode (D-mode).

The main controller 250 may control the pressure device 10 in the blood vessel test so that the user U sequentially contracts or expands the blood vessel of the object Ob and generate the color Doppler image based on the echo ultrasonic signal received through the ultrasonic probe 100.

In addition, the main controller 250 may detect the presence or absence of regurgitation of blood on the plurality of regions based on the generated color Doppler image, and may automatically position the sample volume of the pulse wave. Therefore, the embodiments of the present disclosure will be described below assuming that the C-mode and D-mode are set.

Particularly, the main controller 250 may determine a first region to be operated in based on the position of the ultrasonic probe 100 transmitted by the pressure device 10. When the test of the first region is completed, the main controller 250 operates in the second region of the pressure device 10 based on a predetermined order and time. When the user U places the ultrasonic probe 100 in the third region instead of the second region in the predetermined order, the main controller 250 controls the other region of the pressure device 10 based on the third region.

Various embodiments in which the main controller 250 operates the pressure device 10 will be described below with reference to other figures.

The main controller 250 may determine the presence or absence of regurgitation and the regurgitation occurrence time of the blood in the blood vessel based on the color Doppler image. Here, the regurgitation occurrence time of the blood may be obtained based on a time point when the blood vessel of the object Ob is contracted and then expanded. The disclosed embodiment may be obtained when the pressure device 10 presses the blood vessel of the object Ob.

In addition, the main controller 250 may automatically set the sample volume of the pulse wave based on the obtained color Doppler image, and may calculate the blood flow velocity by analyzing the spectrum of the blood flow in the set sample volume.

Meanwhile, the main controller 250 may be implemented through at least one of the processor and the graphic processor capable of performing various processes such as an image processing process and an arithmetic processing process, or may also be implemented through a single component.

In addition, the ultrasonic diagnostic apparatus 1 may include various configurations other than those described above, and at least one component may be added or deleted corresponding to the performance of the components. In addition, the mutual position of the components may be changed corresponding to the performance or structure of the system, and is not necessarily limited to the position in FIG. 5.

Figure 6:
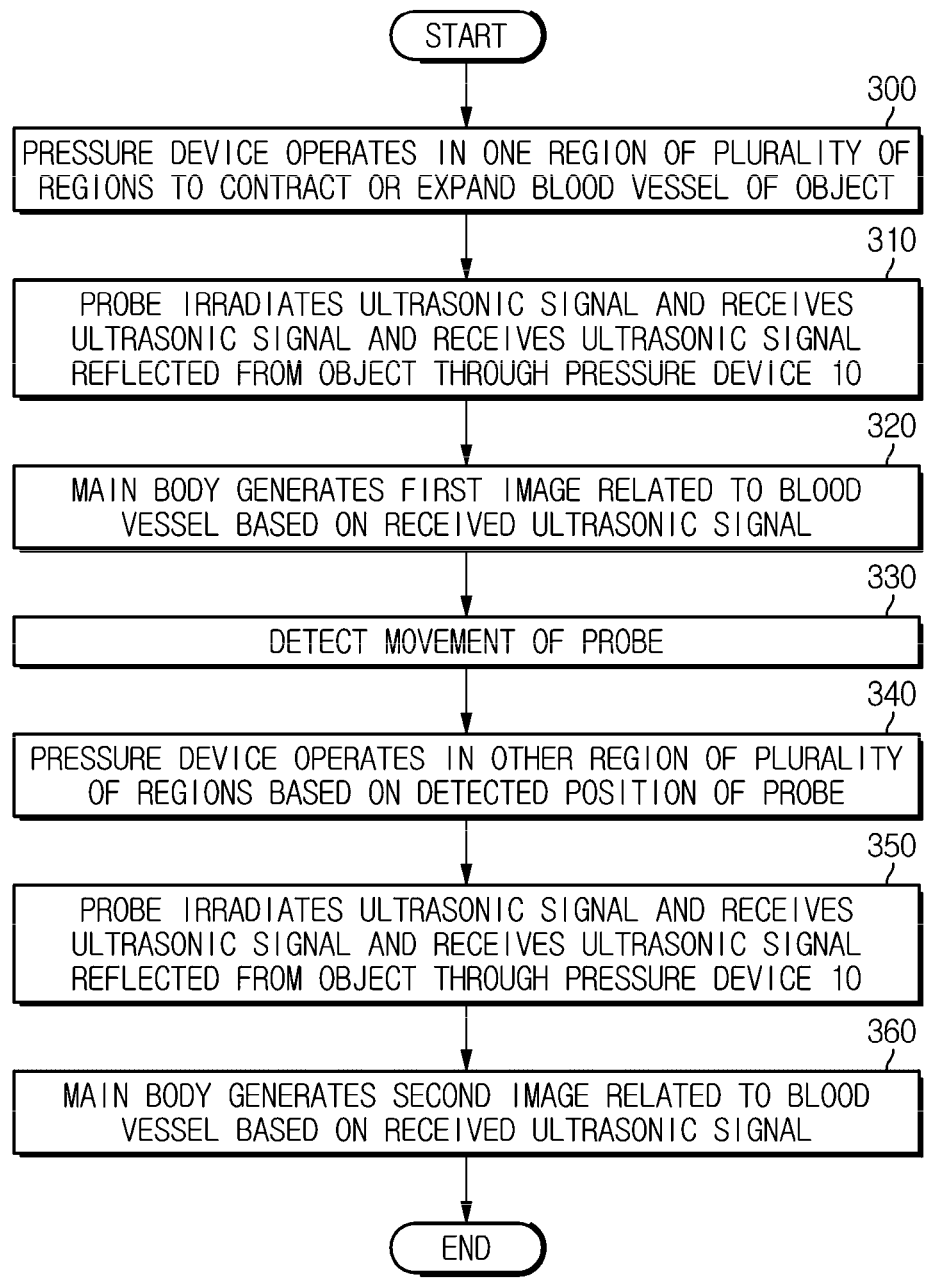
FIG. 6 is a flowchart illustrating a control method of the ultrasonic diagnostic apparatus according to an embodiment.

FIG. 6 is a flowchart illustrating a control method of the ultrasonic diagnostic apparatus according to an embodiment.

Referring to FIG. 6, the pressure device 10 may operate in one of the plurality of regions to contract or expand the blood vessel of the object Ob (300).

The way in which the pressure device 10 contracts or expands the blood vessel of the object Ob may vary. For example, the pressure device 10 may expand or contract one region of the plurality of regions by using at least one of air, fluid, and oil, or contract or expand the blood vessel of the object Ob through the electrical method using the voltage.

The ultrasonic probe 100 may irradiate the ultrasonic signal and receive the echo ultrasonic signal reflected from the object Ob through the pressure device 10 (310).

In the disclosed embodiment, one of the plurality of regions is determined to be the region where the ultrasonic probe 100 is positioned in the pressure device 10. That is, in order to determine whether the blood vessel is regurgitated, the pressure device 10 operates in the lower region in the region where the ultrasonic probe 100 is positioned. A detailed description thereof will be given later with reference to FIG. 7 and the like.

Therefore, the ultrasonic signal irradiated by the ultrasonic probe 100 may be irradiated to the object Ob through the pressure device 10, and the ultrasonic probe 100 may receive the echo ultrasonic signal reflected from the object Ob through the pressure device 10.

The main body 200 may generate a first image related to the blood vessel based on the received ultrasonic signal (320).

As described above with reference to FIG. 5 and the like, the first image relates to motion-related blood flow and may be the color Doppler image. In addition, the main body 200 may generate the first image, and determine the presence or absence of regurgitation of blood flow and the regurgitation occurrence time based on the generated image. Also, the main body 200 may automatically analyze the blood flow spectrum of the sample volume by automatically setting the sample volume of the pulse wave in the color Doppler image.

After the process related to the generated first image, the pressure device 10 may detect movement of the ultrasonic probe 100 (330).

In one example, the pressure device 10 may detect the pressure of the ultrasonic probe 100 in the first region. After the first image is generated, the pressure device 10 may detect the pressure of the ultrasonic probe 100 in the second region instead of the first region.

The main body 200 may control the pressure device 10 to operate in the other of the plurality of regions based on the detected position of the ultrasonic probe 100 (340).

For example, the other region to be operated in among the plurality of regions may be a region other than the region where the ultrasonic probe 100 is positioned.

When the pressure device 10 expands or contracts the blood vessel through the other region, the ultrasonic probe 100 may irradiate the ultrasonic signal and receive the echo ultrasonic signal reflected from the object Ob (350).

The main body 200 may generate a second image related to the blood vessel based on the received ultrasonic signal (360).

That is, the ultrasonic diagnostic apparatus 1 may determine the operating region of the pressure device 10 sequentially based on the position of the ultrasonic probe 100.

Figure 7:
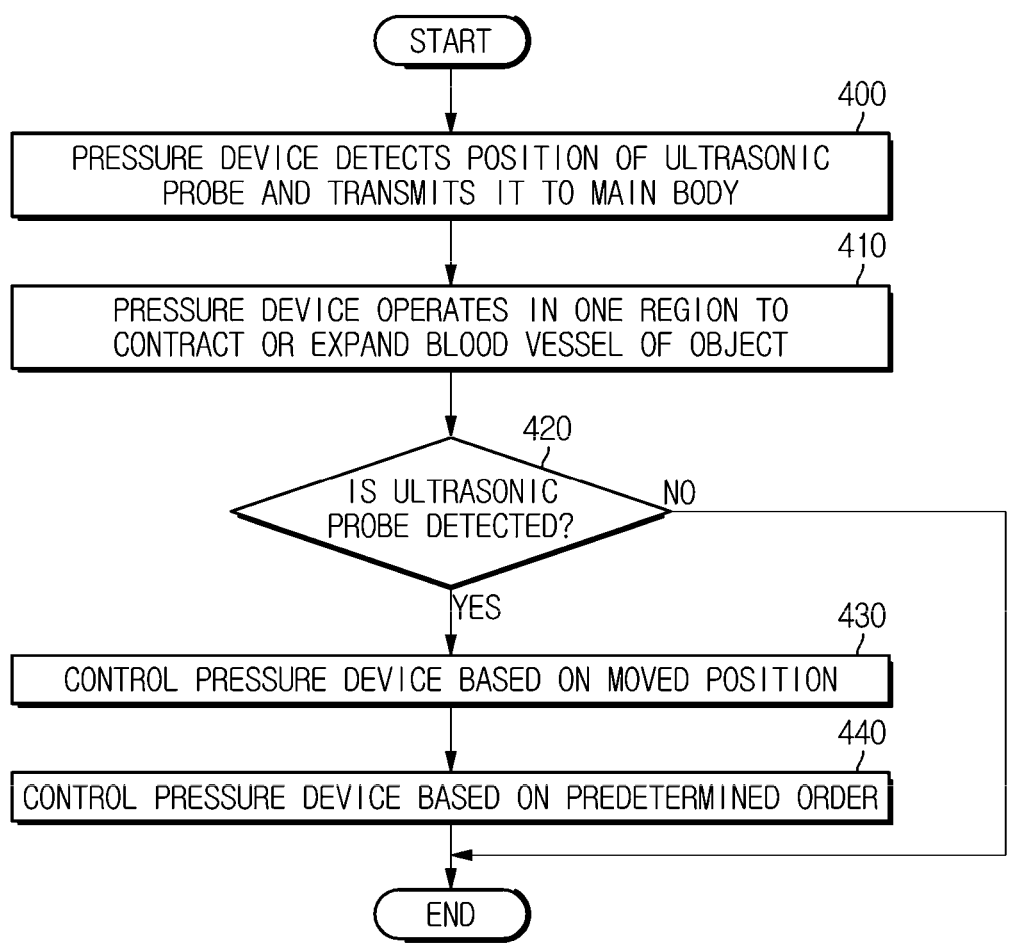
FIG. 7 is a flowchart for describing an operation of the ultrasonic diagnostic apparatus in more detail.

FIG. 7 is a flowchart for describing an operation of the ultrasonic diagnostic apparatus in more detail, and FIGS. 8A to 8D are views for supplementing the procedure of FIG. 7. FIG. 7 and FIGS. 8A to 8D will be described together to avoid redundant explanations.

Referring to FIG. 7, the pressure device 10 may detect the position of the ultrasonic probe 100 and transmit it to the main body 200 (400).

Figure 8A:
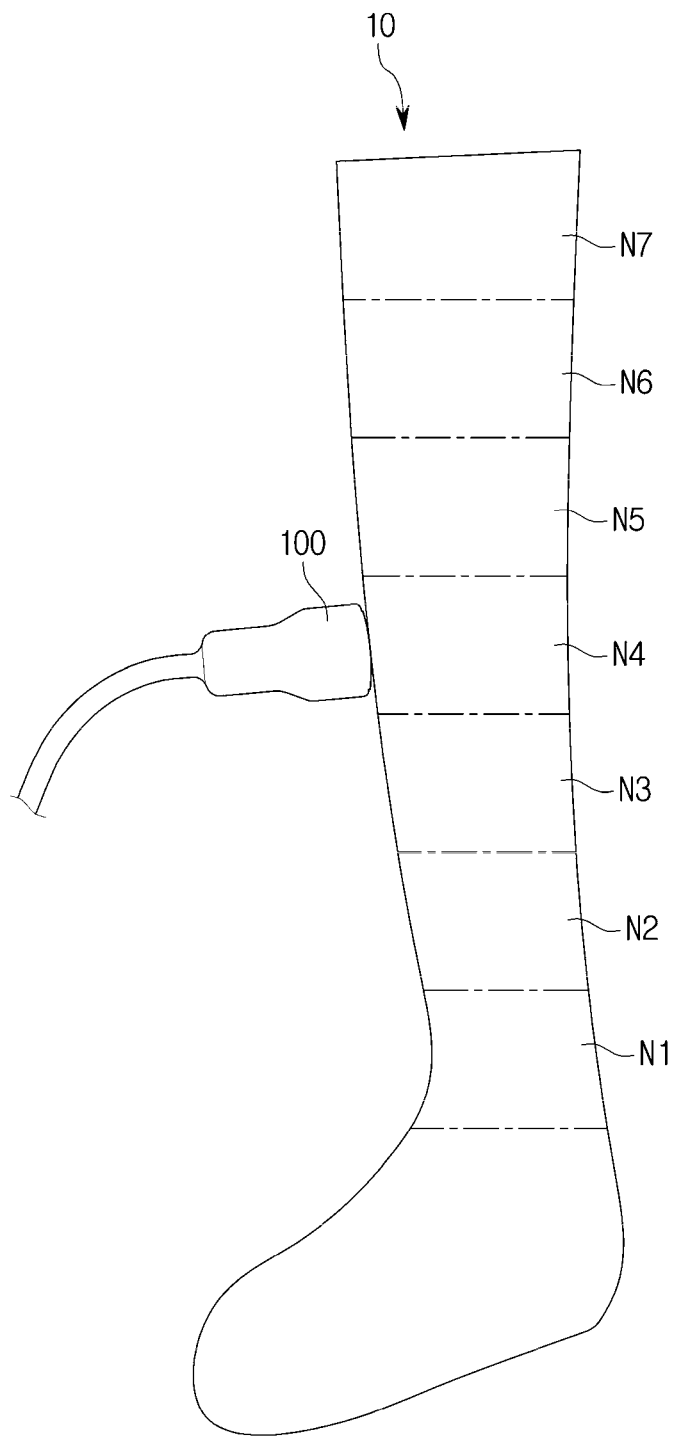
FIGS. 8A to 8D are views for supplementing the procedure of FIG. 7.

For example, as illustrated in FIG. 8A, the ultrasonic probe 100 may be positioned in one of a plurality of regions N1 to N7 divided in the pressure device 10. The pressure device 10 may detect the pressure of the ultrasonic probe 100 and may transmit it to the main body 200.

The pressure device 10 may operate in one region to contract or expand the blood vessel of the object Ob (410).

Figure 8B:
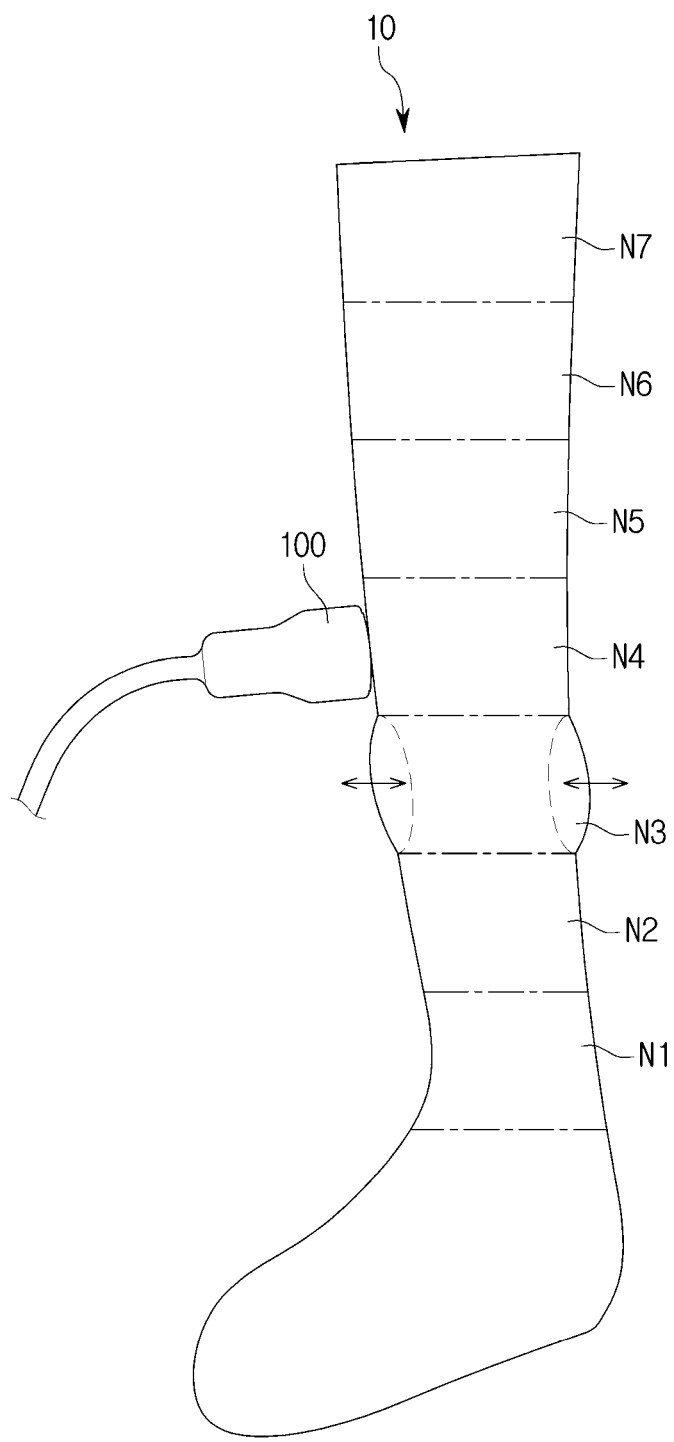

As illustrated in FIG. 8B, the pressure device 10 may operate in the region N3 positioned under the region N4 where the ultrasonic probe 100 is positioned to contract or expand the blood vessel.

On the other hand, as described above with reference to FIG. 5 and the like, in the ultrasonic diagnostic apparatus 1, the order of the blood vessel test may be preset by the guide program or the like. Accordingly, after one region of the pressure device 10 is operated in, the ultrasonic diagnostic apparatus 1 may determine where the ultrasonic probe 100 is positioned based on the predetermined order (420).

If the ultrasonic probe 100 is detected in a region corresponding to the predetermined order, the ultrasonic diagnostic apparatus 1 operates the pressure device 10 based on the predetermined order.

For example, after the operation of FIG. 8B, if the ultrasonic probe 100 is detected in the N5 region, the ultrasonic diagnostic apparatus 1 may operate in the N6 region of the pressure device 10.

However, when the ultrasonic probe 100 is not detected in the region corresponding to the predetermined order, the ultrasonic diagnostic apparatus 1 operates the pressure device 10 based on the detected region.

Figure 8C:
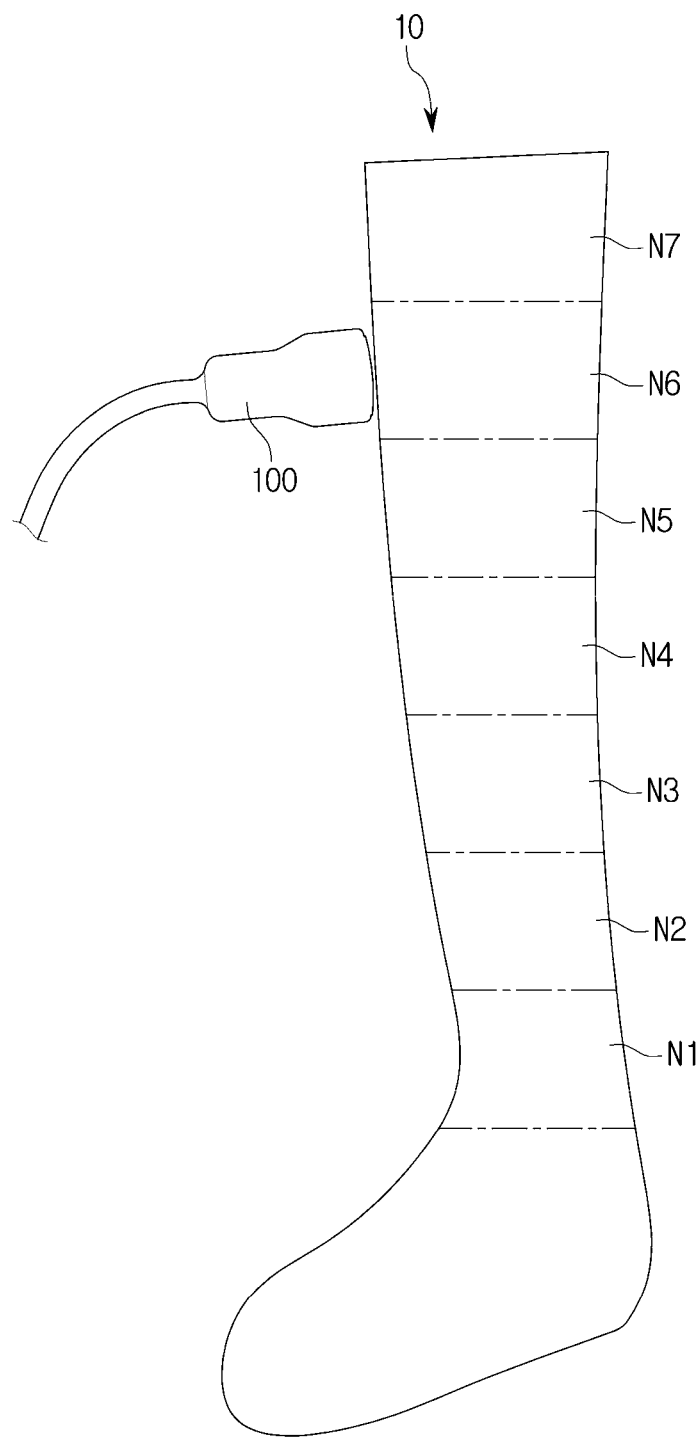
Figure 8D:
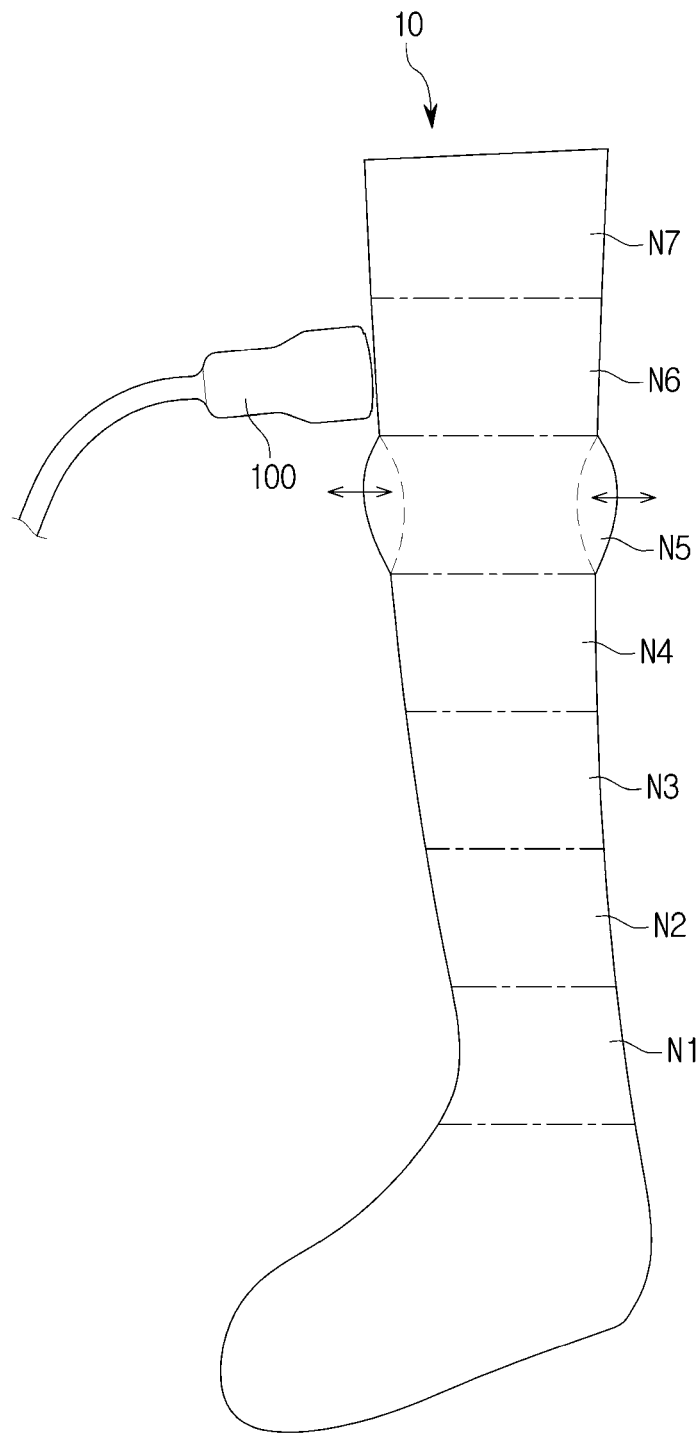

For example, the ultrasonic probe 100 may be moved to the N6 region and detected as illustrated in FIG. 8C. In this case, the ultrasonic diagnostic apparatus 1 may operate in the N5 region of the pressure device 10 to contract or expand the blood vessel as illustrated in FIG. 8D.

Figure 9:
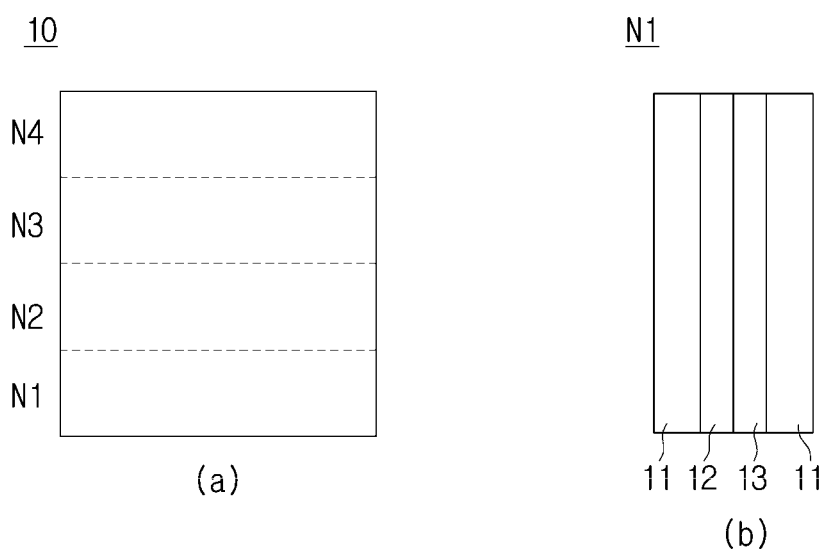
FIG. 9 is a view illustrating one part of the pressure device according to an embodiment.
Figure 10:
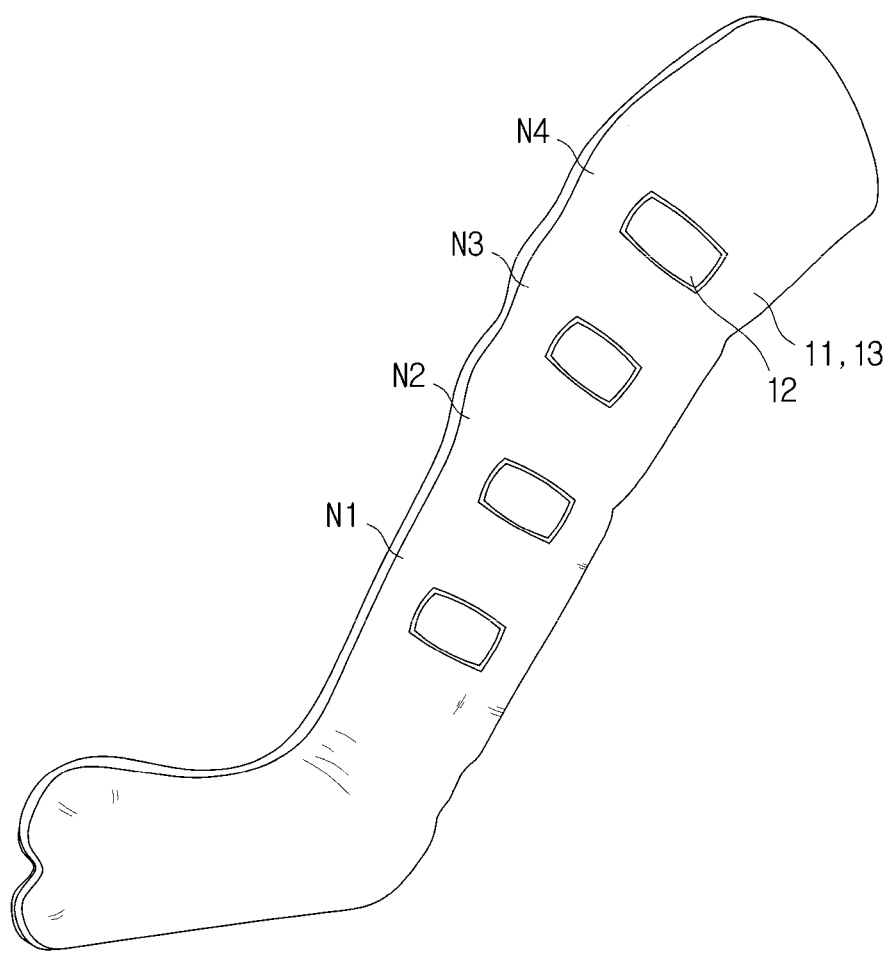
FIG. 10 is a view illustrating an appearance of a detector provided only in one part according to another embodiment.

FIG. 9 is a view illustrating one part of the pressure device according to an embodiment, and FIG. 10 is a view illustrating an appearance of a detector provided only in one part according to another embodiment. FIG. 9 and FIG. 10 will be described together to avoid redundant explanations.

First, FIG. 9A is an external view of the pressure device 10 viewed from the side, and the pressure device 10 may be divided into a plurality of the regions N1 to N4.

FIG. 9B is a cross-sectional view of one of the plurality of regions. The pressure device 10 may include a gel pad 11 formed of a material through which the ultrasonic signal can pass, the detector 12 for detecting the pressure generated by the ultrasonic probe 100 and the operator 13 for contracting or expanding the blood vessel.

The pressure device 10 according to the embodiment may include the detector 12 disposed on a whole region of the plurality of regions to detect the ultrasonic probe 100 regardless of where the user U places the ultrasonic probe 100.

Conversely, referring to FIG. 10, the pressure device 10 according to another embodiment may detect the ultrasonic probe 100 only in one portion and may be provided with an indication or shape that guides the user U to position the ultrasonic probe 100 at the exterior.

On the other hand, similarly in the embodiment of FIG. 10, the pressure device 10 may include the gel pad 11 through which the ultrasonic signal can pass and the operator 13 which contracts or expands the blood vessel.

Figure 11:
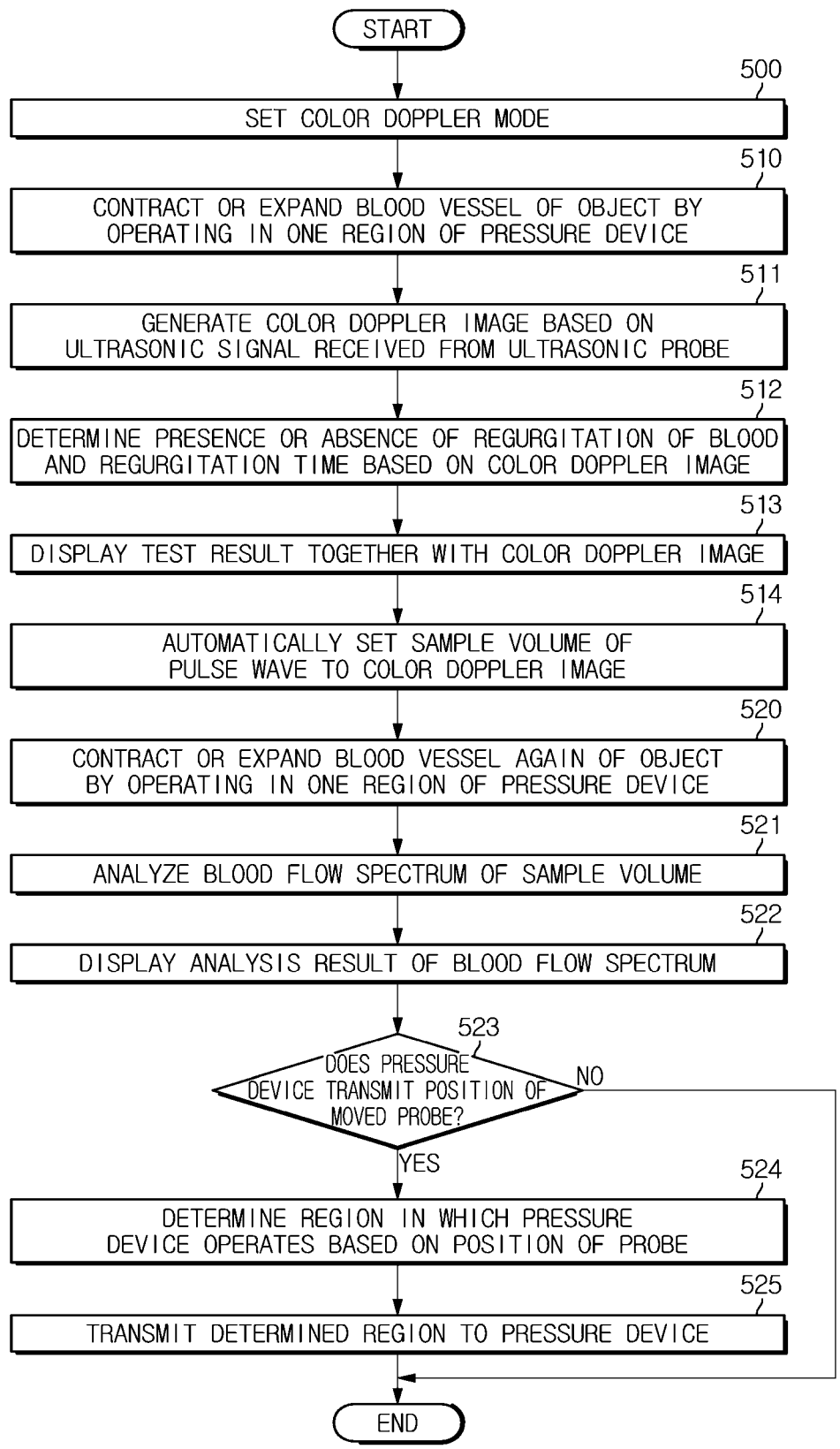
FIG. 11 is a flowchart for describing a method in which the ultrasonic diagnostic apparatus performs a blood vessel test in one area of the pressure device.
Figure 12:
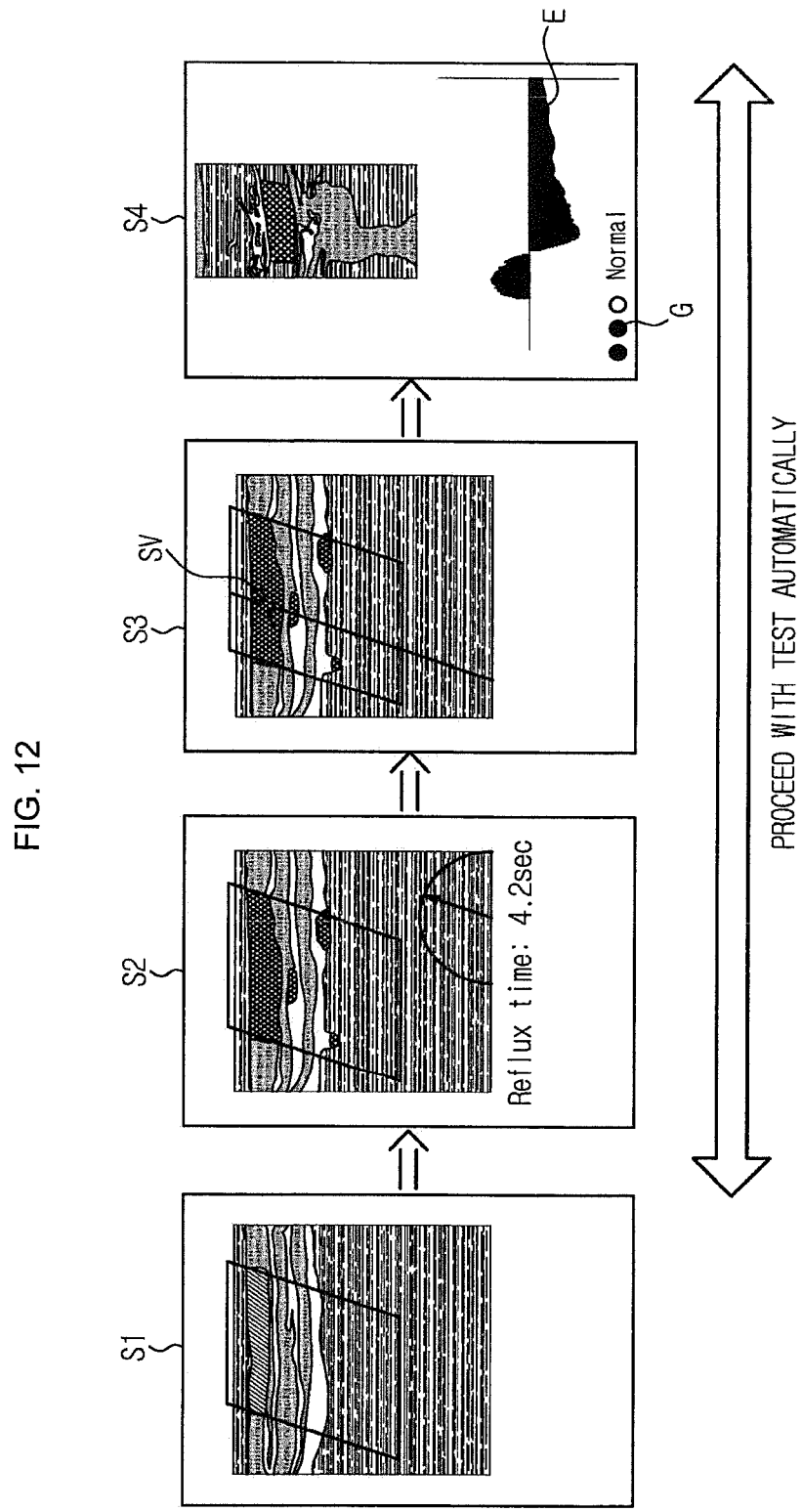
FIG. 12 is a view illustrating the flowchart of FIG. 11 as a workflow.

FIG. 11 is a flowchart for describing a method in which the ultrasonic diagnostic apparatus performs a blood vessel test in one area of the pressure device, and FIG. 12 is a view illustrating the flowchart of FIG. 11 as a workflow. FIG. 11 and FIG. 12 will be described together to avoid redundant explanations.

Referring to FIGS. 11 and 12, the ultrasonic diagnostic apparatus 1 may set the color Doppler mode (500).

For example, the user U may input an execution command for the color Doppler mode through the inputter 240, and may set a color box CB in the B-mode image. The ultrasonic diagnostic apparatus 1 may operate in the color Doppler mode based on the execution command transmitted from the inputter 240.

The pressure device 10 may operate in one region to contract or expand the blood vessel of the object Ob (510). The ultrasonic diagnostic apparatus 1 may generate the color Doppler image based on the ultrasonic signal received from the ultrasonic probe 100 (511).

When the ultrasonic diagnostic apparatus 1 operates in the color Doppler mode, the ultrasonic probe 100 may generate the color Doppler image based on the received echo ultrasonic signal. Particularly, the ultrasonic diagnostic apparatus 1 may obtain a Doppler signal corresponding to the color box CB set by the user U and generate the color Doppler image based on the obtained Doppler signal.

A first screen S1 of FIG. 12 illustrates an example of entry into the color Doppler mode provided to the display 260 of the main body 200 when the ultrasonic diagnostic apparatus 1 enters the color Doppler mode.

When the ultrasonic diagnostic apparatus 1 enters the color Doppler mode and operates the pressure device 10, regurgitation of the blood vessel occurs, and the ultrasonic probe 100 may obtain the Doppler signal generated by regurgitation of the blood and the color Doppler image may be formed based on the obtained Doppler signal.

The ultrasonic diagnostic apparatus 1 may determine the presence or absence of regurgitation of the blood and the regurgitation time based on the generated color Doppler image (512), and display the test result together with the color Doppler image (513).

Particularly, the ultrasonic diagnostic apparatus 1 may determine whether or not the blood is regurgitated based on the color change of the image generated by the operation of the pressure device 10. In addition, the ultrasonic diagnostic apparatus 1 may determine the regurgitation time based on the operation time of the pressure device 10. Here, the operation time may be preset.

A second screen S2 of FIG. 12 illustrates an example of displaying the results of the above-described color Doppler image change, the presence or absence of regurgitation of the blood, and the regurgitation time. In other words, the user U may intuitively confirm the presence or absence of regurgitation of the blood through the color change of the color Doppler image, and the ultrasonic diagnostic apparatus 1 may display graphics or text together to visually provide the results of the presence or absence of regurgitation of the blood, and the regurgitation time.

Thereafter, the ultrasonic diagnostic apparatus 1 may automatically set the sample volume of the pulse wave to the color Doppler image based on the color Doppler image (514).

This process may be performed automatically after the provision of the second screen S2 of FIG. 12 according to the setting of the user U, thereby simplifying the test process of the user U.

Particularly, a third screen S3 of FIG. 12 may be provided after a predetermined time has elapsed after the second screen S2 is provided. The method of automatically setting a sample volume SV of the pulse wave may include a method of randomly setting the sample volume and may be a method of setting the sample volume at the central portion of the color Doppler image according to the embodiment, but is not limited to.

When the sample volume is set, the ultrasonic diagnostic apparatus 1 may again operate in one region of the pressure device 10 to contract or expand the blood vessel of the object Ob (520).

The ultrasonic diagnostic apparatus 1 may analyze the blood flow spectrum of the sample volume based on the blood flow information obtained by the ultrasonic probe 100 according to the contraction or expansion of the blood vessel (521) and display the analysis result of the blood flow spectrum (522).

In a fourth screen S4 of FIG. 12, a blood flow spectrum E for visually providing the test result together with the color Doppler image may be provided. The blood flow spectrum may be provided in the form of a graph including the blood flow velocity and blood flow direction information, and the user U may determine the blood flow velocity, for example, the maximum velocity, the average velocity, and the minimum velocity and the direction information of the blood flow through the blood flow spectrum.

In addition, the ultrasonic diagnostic apparatus 1 may also display a diagnostic grade G for the detected regurgitation time. For example, the range of the detected regurgitation time may be divided into stages, and the diagnostic grade may be classified into low risk, normal, and high risk according to the range. The range of the diagnostic grade may be preset.

After proceeding to the above-described procedure, the ultrasonic diagnostic apparatus 1 may wait until the pressure device 10 receives the result of detecting the position of the moved ultrasonic probe 100 (523).

When the pressure device 10 transmits the result of the position of the ultrasonic probe 100 being moved, the ultrasonic diagnostic apparatus 1 may determine the region in which the pressure device 10 will operate in based on the detected position (524).

When the region to be operated in is determined, the ultrasonic diagnostic apparatus 1 may control the pressure device 10 based on the determined region (525), and repeat the process of 500 and subsequent again.

Figure 13:
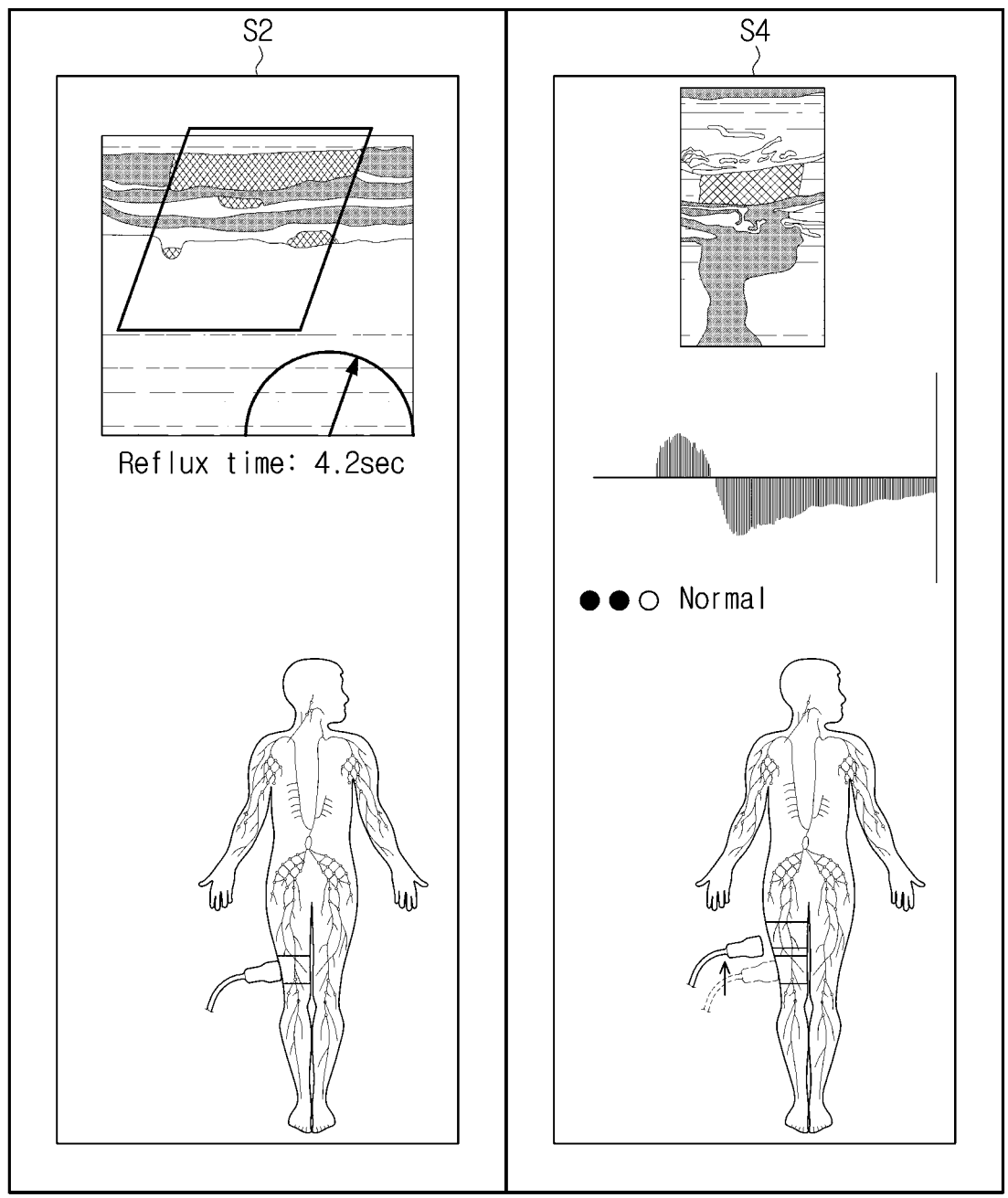
FIG. 13 is a view illustrating an interface according to another embodiment.

FIG. 13 is a view illustrating an interface according to another embodiment.

The ultrasonic diagnostic apparatus 1 may shape and display the region N1 and the object Ob in which the current ultrasonic probe 100 is positioned on the second screen S2 on which the color Doppler image and the regurgitation time are displayed.

That is, the ultrasonic diagnostic apparatus 1 may determine one region of the pressure device 10 in which the ultrasonic probe 100 is positioned, and display the position of the ultrasonic probe 100 determined based on the contact region of the ultrasonic probe 100.

Also, the ultrasonic diagnostic apparatus 1 may display the region N2 where the next ultrasonic probe 100 can be positioned and the region N1 of the object Ob in which the current image is displayed on the fourth screen S4 on which the blood spectrum is displayed by using the sample volume to induce the user U to proceed with the examination.

Meanwhile, FIGS. 12 and 13 are examples of screens displayed on the display 260 according to the embodiment, but the present disclosure is not limited thereto, and various modified examples may be applied.

Figure 14:
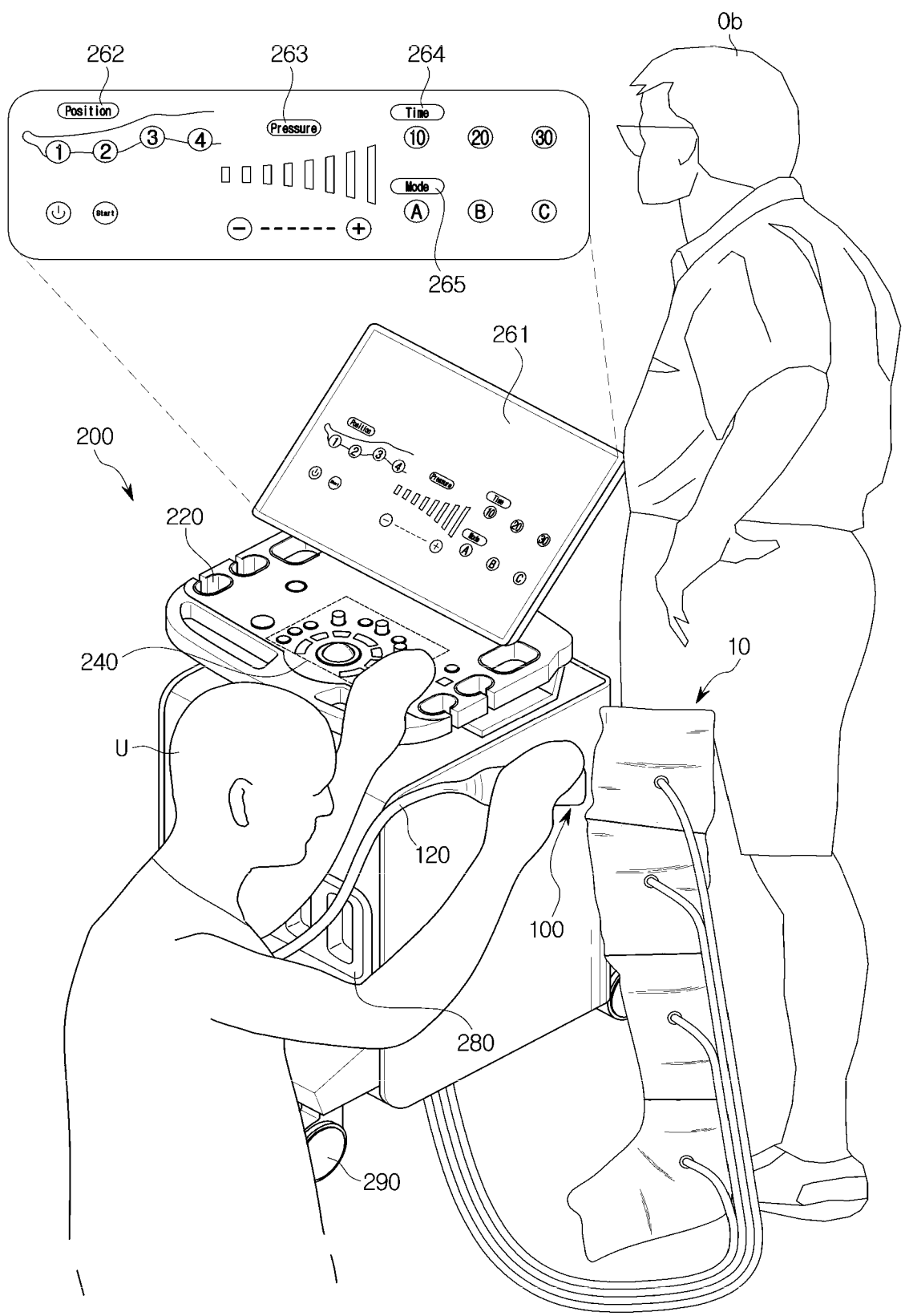
FIG. 14 is a view illustrating an example in which the ultrasonic diagnostic apparatus displays a user interface associated with the pressure device.

FIG. 14 is a view illustrating an example in which the ultrasonic diagnostic apparatus displays a user interface associated with the pressure device.

Referring to FIG. 14, the ultrasonic diagnostic apparatus 1 may display a user interface associated with the operation of the pressure device 10 on the auxiliary display 261 before the pressure device 10 operates in one region.

Particularly, the ultrasonic diagnostic apparatus 1 may display a first user interface 262 relating to the operation order of the plurality of regions included in the pressure device 10 by the user U. The first user interface 262 may include a number indicating the operation order along with a shape corresponding to a test region of the blood vessel test. The user U may adjust the operating region of the pressure device 10 by adjusting the order.

In addition, the ultrasonic diagnostic apparatus 1 may display a second user interface 263 relating to a pressure (contraction strength, expansion strength) for contracting or expanding the blood vessel of the object Ob. Through this second user interface 263, the user U may adjust the contraction strength and the expansion strength by touching the inputter 240 or the auxiliary display 261.

The ultrasonic diagnostic apparatus 1 may display a third user interface 264 relating to the operation time (contraction time, expansion time) of the pressure device 10 when the blood vessel is contracted or expanded. For example, the ultrasonic diagnostic apparatus 1 may display a plurality of preset operating times to facilitate input of the user U.

The ultrasonic diagnostic apparatus 1 may designate the above-described operation order, contraction or expansion intensity, and contraction or expansion time as a plurality of modes 265 and display it to the user U. The user U may store frequently used setting commands in each mode and may easily input various user interfaces by selecting the mode 265.

The user interface described above with reference to FIG. 14 may be provided by the ultrasonic diagnostic apparatus 1 so that the user U can easily control the pressure device 10. Therefore, the present disclosure is not limited to the example of FIG. 14, and various modified examples may be made.

As is apparent from the above description, the disclosed ultrasonic diagnostic apparatus and the control method thereof recognize the position of the probe and sequentially press the part of the object according to the workflow, thereby making it possible to eliminate the user's inconvenience and shorten the vascular regurgitation test time.

Although exemplary embodiments of the present disclosure have been described for illustrative purposes, those skilled in the art will appreciate that various modifications, additions and substitutions are possible, without departing from the scope and spirit of the disclosure. Therefore, exemplary embodiments of the present disclosure have not been described for limiting purposes.

What is claimed is:

1. An ultrasonic diagnostic apparatus comprising:
   a probe configured to irradiate an ultrasonic signal to an object and receive the ultrasonic signal reflected from the object;
   a pressure device configured to contract or expand a blood vessel of the object and configured to be divided into a plurality of regions; and
   a controller configured to operate in one region of the plurality of regions to generate an image related to the blood vessel of the object and sequentially operate in other regions of the plurality of regions,
   wherein the pressure device comprises a detector configured to detect a pressure transmitted by the probe, and
   the controller is configured to determine the one region of the pressure device based on a contact region of the probe transmitted by the detector.

2. The ultrasonic diagnostic apparatus according to claim 1, wherein the pressure device is provided with a material capable of transmitting the ultrasonic signal irradiated by the probe.

3. The ultrasonic diagnostic apparatus according to claim 1, wherein the pressure device is configured to contract or expand the blood vessel using at least one of voltage, air, fluid and oil.

4. The ultrasonic diagnostic apparatus according to claim 1, wherein the controller is configured to generate a color Doppler image based on the ultrasonic signal transmitted by the probe and determine the presence or absence of regurgitation of blood and the regurgitation occurrence time based on the generated color Doppler image.

5. The ultrasonic diagnostic apparatus according to claim 4, wherein the controller is configured to sequentially operate in the other regions of the plurality of regions based on a predetermined order and time after the color Doppler image is generated.

6. The ultrasonic diagnostic apparatus according to claim 1,
   wherein the controller is configured to determine a position of the pressure device based on a user input.

7. The ultrasonic diagnostic apparatus according to claim 1, wherein the controller is configured to change the order of operating the other regions of the plurality of regions based on a user input.

8. The ultrasonic diagnostic apparatus according to claim 1, wherein the controller is configured to adjust at least one of operation order, contraction strength, contraction time, expansion strength and expansion time of the pressure device based on a user input.

9. The ultrasonic diagnostic apparatus according to claim 1, further comprising:
   a display configured to display the generated image, and
   wherein the display is configured to display a position of the probe determined based on the contact region of the probe.

10. A control method of an ultrasonic diagnostic apparatus which comprises a pressure device divided into a plurality of regions, the method comprising:
    controlling the pressure device so that one region of the plurality of regions contracts or expands a blood vessel of an object;
    irradiating an ultrasonic signal to the object and receiving the ultrasonic signal reflected from the object;
    generating an image related to the blood vessel of the object based on the received ultrasonic signal; and
    re-controlling the pressure device so that other regions of the plurality of regions are sequentially operated in, wherein the pressure device comprises a detector configured to detect a pressure transmitted by a probe, and the controlling comprises determining the one region of the pressure device based on a contact region of the probe transmitted by the detector.

11. The method according to claim 10, wherein the pressure device is provided with a material capable of transmitting the ultrasonic signal.

12. The method according to claim 10, wherein the pressure device is configured to contract or expand the blood vessel using at least one of voltage, air, fluid and oil.

13. The method according to claim 10, wherein the generating comprises:

generating a color Doppler image based on the ultrasonic signal; and determining the presence or absence of regurgitation of blood and the regurgitation occurrence time based on the generated color Doppler image.

14. The method according to claim 13, wherein the controlling comprises:

re-controlling the pressure device to sequentially operate in the other regions of the plurality of regions based on a predetermined order and time after the color Doppler image is generated.

15. The method according to claim 10, further comprising:

receiving an input command related to a test part of the object, and wherein the controlling comprises:

determining a position of the pressure device based on the test part.

16. The method according to claim 10, wherein the controlling comprises:

changing the order of operating the other regions of the plurality of regions based on a user's command.

17. The method according to claim 10, wherein the controlling comprises:

adjusting at least one of operation order, contraction strength, contraction time, expansion strength and expansion time of the pressure device based on a user's command.

18. The method according to claim 10, further comprising:

displaying the generated image, and wherein the displaying comprises:

displaying a position of the probe determined based on the contact region.

* * * * *